(12) United States Patent
Livney

(10) Patent No.: US 9,950,003 B2
(45) Date of Patent: Apr. 24, 2018

(54) PECTIN BASED NANOPARTICLES

(71) Applicant: TECHNION RESEARCH & DEVELOPMENT FOUNDATION LTD., Haifa (IL)

(72) Inventor: Yoav Livney, Misgav (IL)

(73) Assignee: TECHNION RESEARCH & DEVELOPMENT FOUNDATION LTD., Haifa (IL)

( * ) Notice: Subject to any disclaimer, the term of this patent is extended or adjusted under 35 U.S.C. 154(b) by 0 days.

(21) Appl. No.: 15/102,959

(22) PCT Filed: Dec. 11, 2014

(86) PCT No.: PCT/IL2014/051082
§ 371 (c)(1),
(2) Date: Jun. 9, 2016

(87) PCT Pub. No.: WO2015/087329
PCT Pub. Date: Jun. 18, 2015

(65) Prior Publication Data
US 2017/0014445 A1  Jan. 19, 2017

Related U.S. Application Data

(60) Provisional application No. 61/915,019, filed on Dec. 12, 2013.

(51) Int. Cl.
| | | |
|---|---|---|
| *A61K 31/732* | (2006.01) | |
| *A61K 9/00* | (2006.01) | |
| *A61K 31/12* | (2006.01) | |
| *A23L 33/155* | (2016.01) | |
| *A23L 2/52* | (2006.01) | |
| *A23L 29/231* | (2016.01) | |
| *A23L 33/105* | (2016.01) | |
| *A61K 9/51* | (2006.01) | |
| *A61K 45/06* | (2006.01) | |
| *A23D 7/005* | (2006.01) | |
| *A23D 9/05* | (2006.01) | |
| *A61K 31/05* | (2006.01) | |
| *A61K 31/07* | (2006.01) | |
| *A61K 31/122* | (2006.01) | |
| *A61K 31/352* | (2006.01) | |
| *A61K 31/355* | (2006.01) | |
| *A61K 31/592* | (2006.01) | |
| *A61K 31/775* | (2006.01) | |
| *A23L 33/10* | (2016.01) | |
| *A23L 33/15* | (2016.01) | |
| *B82Y 40/00* | (2011.01) | |
| *B82Y 5/00* | (2011.01) | |
| *B82Y 30/00* | (2011.01) | |

(52) U.S. Cl.
CPC .......... *A61K 31/732* (2013.01); *A23D 7/0053* (2013.01); *A23D 9/05* (2013.01); *A23L 2/52* (2013.01); *A23L 29/231* (2016.08); *A23L 33/10* (2016.08); *A23L 33/105* (2016.08); *A23L 33/15* (2016.08); *A23L 33/155* (2016.08); *A61K 9/0095* (2013.01); *A61K 9/5161* (2013.01); *A61K 31/05* (2013.01); *A61K 31/07* (2013.01); *A61K 31/12* (2013.01); *A61K 31/122* (2013.01); *A61K 31/352* (2013.01); *A61K 31/355* (2013.01); *A61K 31/592* (2013.01); *A61K 31/775* (2013.01); *A61K 45/06* (2013.01); *A23V 2002/00* (2013.01); *B82Y 5/00* (2013.01); *B82Y 30/00* (2013.01); *B82Y 40/00* (2013.01)

(58) Field of Classification Search
CPC .. A61K 31/732; A61K 9/0095; A61K 9/5161; A61K 31/05; A61K 31/07; A61K 31/12; A61K 31/122; A61K 31/353; A61K 31/355; A61K 31/775; A61K 31/592; A61K 45/06; A23L 29/231; A23L 33/10; A23L 33/105; A23L 33/15; A23L 33/155; A23D 7/0053; A23D 9/05
See application file for complete search history.

(56) References Cited

U.S. PATENT DOCUMENTS

2011/0274812 A1* 11/2011 Nakauma ............. A23L 1/0524
426/577

FOREIGN PATENT DOCUMENTS

| WO | 2007000193 A1 | 1/2007 |
| WO | WO 2008/140507 | * 11/2008 |
| WO | 2010149759 A1 | 12/2010 |

OTHER PUBLICATIONS

"Beta-lactoglobulin and its nanocomplexes with pectin as vehicles for ω-3 polyunsaturated fatty acids", Food Hydrocolloids, vol. 23, Issue 4, Jun. 2009, pp. 1120-1126, Patricia Zimet a,b, Yoav D. Livney a,b. Jun. 30, 2009.

(Continued)

*Primary Examiner* — Johann R Richter
*Assistant Examiner* — Genevieve S Alley
(74) *Attorney, Agent, or Firm* — The Roy Gross Law Firm, LLC; Roy Gross

(57) ABSTRACT

This invention provides (a) nanoparticle made of: sugar-beet pectin; and a bioactive compound (such as a nutraceutical or a drug) bound to sugar-beet pectin. The invention further provides foods, beverages, including clear ones, or pharmaceutical preparations, which are supplemented with the nanoparticles made of: sugar-beet pectin; and a hydrophobic bioactive compound bound to sugar-beet pectin. The process of making the nanoparticles of the invention, and methods for supplementing foods or beverages or pharmaceutical preparations with bioactive compounds via the nanoparticles of the invention are also provided.

15 Claims, 2 Drawing Sheets

(56) References Cited

OTHER PUBLICATIONS

"Sugar beet pectin: A novel emulsifying wall component for microencapsulation of lipophilic food ingredients by spray-drying", Food Hydrocolloids, vol. 21, Issue 7, Oct. 2007, pp. 1223-1228, Stephan Drusch. Oct. 7, 2007.
"On the determination of the critical micelle concentration by the pyrene 1:3 ratio method", Journal of Colloid and Interface Science, vol. 258, Issue 1, Feb. 2003, pp. 116-122, J. Aguiar. Feb. 1, 2003.
International Search Report for PCT/IL2014/051082 Completed: Mar. 25, 2014; dated Mar. 26, 2014 9 pages.

* cited by examiner

PECTIN BASED NANOPARTICLES

FIELD OF INVENTION

This invention is directed to, inter alia, (1) a nanoparticle comprising: pectin; and a bioactive compound bound to, entrapped or encapsulated within the pectin, and (2) beverages or foods supplemented with the nanoparticles.

BACKGROUND OF THE INVENTION

Preventive medicine consists of measures taken to reduce the risk of diseases, including avoiding smoking, performing physical exercises and following prudent dietary recommendations.

Recently, there is an increasing awareness that food may be either harmful or beneficial to health. This is based in part on a growing scientific understanding of the disease-preventive properties of foods, and in particular certain food components, known as nutraceuticals, such as vitamins, omega-3 fatty acids, certain minerals and certain phytochemicals. Nutraceuticals are health-promoting bioactives. They have been associated with the prevention and/or treatment of disorders like cardio-vascular disease, cancer, hypertension, diabetes, osteoporosis, arthritis etc.

One way to increase the consumption of health promoting bioactives is to enrich foods and beverages that people normally consume with nutraceuticals. However, enriching foods with nutraceuticals may pose great challenges, especially when the nutraceuticals are poorly water-soluble, and are easily degradable.

The solubilization of hydrophobic health-promoting bioactives in clear drinks is highly sought by beverage producers to provide added value for the consumer, but it still poses tough challenges, particularly in shelf stable drinks. Most food grade surfactants, which may be used for the task are synthetic e.g. the Tween (polysorbate) series, and thus preclude an "all-natural ingredients" labeling. Other ways to enrich beverages with hydrophobic nutraceuticals, like gum Arabic, milk proteins, soybean proteins and Maillard reaction conjugates are either expensive, not always available, or are using allergenic components.

Clear drinks, which are consumed in large quantities, pose a particularly important challenge because of the difficulty of incorporating oil-soluble materials in a clear and stable aqueous system. The ideal vehicle for the task should be nano-sized to maintain transparency, preferably ≤100 nm, and comprised of only natural, generally regarded as safe and inexpensive food components, capable of solubilizing and protecting hydrophobic biologically active molecules in aqueous media while retaining sensory qualities, and promoting bioavailability of hydrophobic biologically active molecules. Very few solutions for these challenging requirements have been suggested and none has all the desired attributes.

Commercial pectins are often derived from citrus and apple pulps. These are characterized by high viscosity of low solids aqueous solutions and form gels in the presence of high solids sucrose solutions and/or calcium under mildly acidic conditions. Historically, commercial pectin production from sugar beet commenced in Europe during World War II but ceased when citrus and apple pulps again became available. Generally, sugar beet pectins were regarded as inferior and their function was enhanced by conversion to low ester pectinic acids which produce ionically crosslinked gels in the presence of polyvalent cations.

Spent sugar beet pulp consists largely of structural polysaccharide complexes associated with the primary cell wall of parenchymatous tissue. Subsequent extraction of spent beet pulp under hydrolytic conditions generates solubilized forms of the non-cellulosic components whose yield and chemical classification vary depending on the severity of hydrolysis condition and the specific extractive method employed.

Nanoencapsulation is a rapidly developing technology which has great potential to overcome solubility limitations, protect sensitive compounds from degradation during production and shelf-life, mask undesired off-flavors, and promote bioavailability of encapsulated nutraceuticals.

Vitamin D and omega 3 were chosen as model hydrophobic nutraceutical compounds. Vitamin D is a fat soluble vitamin that has great importance for calcium and phosphorus homeostasis. VD is also associated with cardiovascular health, cancer prevention, insulin sensitivity, regulation of immune function and decreased risk of autoimmune diseases. $VD_3$ is synthesized in the skin upon exposure to ultraviolet type-B radiation. There are scarce natural dietary sources for VD, including certain fish oils and egg yolk. About 1 billion people worldwide are VD deficient or insufficient, mainly due to avoidance of sun exposure to prevent melanoma, the use of sunscreen which blocks VD synthesis and low dietary intake. Besides its low solubility in water, vitamin D is sensitive to low pH, oxidation and heat.

Omega 3 fatty acids show remarkable preventive-medicine activities: they reduce the risk of cardiovascular diseases and the metabolic syndrome, they lower blood pressure, serum cholesterol and triglyceride levels and they are considered to have antithrombotic, antiatherogenic and antiinflammatory properties. However, omega 3 fatty acids and their ester forms have very low aqueous solubility, and very high sensitivity to oxidation, resulting in undesired odors and flavors.

SUMMARY OF THE INVENTION

In one embodiment, the present invention provides a nanoparticle comprising: (a) sugar-beet pectin; and (b) a bioactive compound bound to, entrapped or encapsulated within sugar-beet pectin. The bioactive compound, in some embodiments, is a compound having maximal aqueous solubility below 1 g/l. The bioactive compound, in some embodiments, is an oil-soluble vitamin, a polyunsaturated fatty acid or its ester, an antioxidant, a phytochemical, an Omega-3 fatty acid, or its esters, or any combination thereof.

In another embodiment, the present invention further provides a composition comprising an aqueous liquid, a bioactive compound, and sugar-beet pectin. In some embodiments, the aqueous liquid is a transparent aqueous liquid such as a clear beverage. In one embodiment, a composition comprising an aqueous liquid, a bioactive compound, and sugar-beet pectin is devoid of an additional emulsifier.

In another embodiment, the present invention further provides a method for supplementing a subject with a bioactive compound, comprising the step of administering to the subject a composition comprising: an aqueous liquid, a bioactive compound, and sugar-beet pectin bound to the bioactive compound, thereby supplementing a subject with a bioactive compound. In some embodiments, the subject is afflicted with a disease requiring essential fatty acids support such as: a cardiovascular disease, a reproductive disease, an immune disease, a nervous system disease, or any combination thereof.

In another embodiment, the present invention further provides a process for preparing a nanoparticle comprising: a sugar-beet pectin; and a bioactive compound bound to, entrapped or encapsulated within sugar-beet pectin, comprising the steps of preparing a first solution, a second solution, a mix of the first solution and the second solution; wherein the first solution is prepared according to the steps of: (a) dissolving sugar-beet pectin in water at a concentration of 0.1 to 100 g/L; (b) stirring the solution obtained in (a) for 10 minutes to 24 hours at 4 to 40° C.; and (c) filtering the solution obtained in (b) through a filter having a cutoff of 0.1 to 1 microns; wherein the second solution is prepared according to the step of: dissolving the bioactive compound in a water-miscible organic food grade solvent; wherein the mix is prepared according to the step of: combining the first solution and the second solution by slowly adding said second solution into the first solution while intensive stirring is applied, thereby preparing a nanoparticle dispersion comprising: sugar-beet pectin; and a bioactive compound bound to, entrapped or encapsulated within sugar-beet pectin.

The nanoparticles of the invention may be dried by any method known in the art, with or without the use of drying aids, such as saccharides, and reconstituted in water or aqueous solution to form a clear stable solution or dispersion.

DETAILED DESCRIPTION OF THE INVENTION

Figure 1:
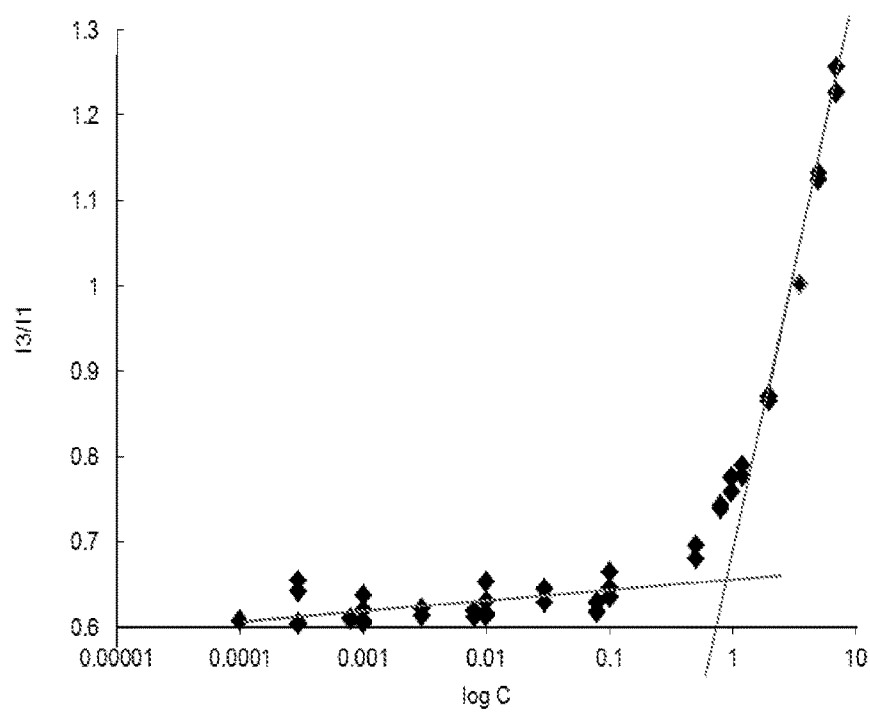
FIG. 1. Is a graph providing estimation of the critical micellization concentration (CMC) of sugar beet pectin (SBP) from the onset of rise in the I3/I1vs fluorescence of pyrene (CMC~1 mg/ml).

In one embodiment, the present invention provides a nanoparticle (or a plurality of nanoparticles) comprising: (a) sugar-beet pectin; and (b) a bioactive compound bound to sugar-beet pectin. In another embodiment, the present invention further provides that the nanoparticle of the invention is a nanocapsule comprising: (a) a nanoshell comprising sugar-beet pectin; and (b) a core comprising a bioactive compound bound to—entrapped in or encapsulated by the sugar-beet pectinnanoshell.

In another embodiment, the present invention further provides that the polysaccharide complex isolated by extractive hydrolysis of spent sugar beet pulp as described herein will be referred to as a pectin, or a modified pectin. In another embodiment, "pectin" or "sugar beet pectin" include pectin and a protein naturally covalently bound to the pectin.

In another embodiment, "a protein naturally covalently bound to the pectin" is a protein bound covalently to the pectin within a wild-type sugar beet plant.

In another embodiment, pectin according to the invention comprises protein, preferably (naturally) covalently bound to the pectin, forming a natural pectin-protein copolymer. In another embodiment, the said protein provides the hydrophobic domain of the natural pectin-protein copolymer, capable of binding the active hydrophobic compound, as can be readily determined by one of skill in the art. In another embodiment, pectin according to the invention comprises 0.5-3.5 weight % protein.

In one embodiment, pectin is a low methoxyl sugar-beet pectin. In another embodiment, pectin is a high methoxyl sugar-beet pectin. In another embodiment, pectin is at least a 40% esterified pectin. In another embodiment, pectin is 40% to 75% esterified pectin. In another embodiment, pectin is 60% to 78% esterified pectin. In another embodiment, sugar-beet pectin is a highly (2-O- and/or 3-O-galacturonic acid backbone) acetylated pectin (such as from sugar beet as described herein). In another embodiment, pectin contains at least 65% by weight of galacturonic acid units.

In another embodiment, the nanoshell consists of a pectin. In another embodiment, the nanoshell comprises an additional polymer. In another embodiment, the additional polymer is a biodegradable polyester polymer. In another embodiment, the additional polymer is Poly-e-caprolactone (PCL). In another embodiment, the additional polymer is poly(lactide) (PLA). In another embodiment, the additional polymer is poly(lactide-co-glicolide) (PLGA). In another embodiment, the additional polymer is poly(methacrylic acid). In another embodiment, the additional polymer is poly(N-vinyl Pyrrolidone). In another embodiment, the additional polymer is a synthetic polymer. In another embodiment, the additional polymer is a natural polymer. In another embodiment, the additional polymer is a polysaccharide. In another embodiment, the additional polymer is chitosan. In another embodiment, the additional polymer is gelatin. In another embodiment, the additional polymer is sodium alginate. In another embodiment, the additional polymer is albumin. In another embodiment, the nanoshell comprises a polysaccharide. In another embodiment, the nanoshell comprises a saccharide.

In another embodiment, the present invention further provides that a nanocapsule encapsulates an inner liquid core, a solid core, or a partly liquid and partly solid core. In another embodiment, the present invention further provides that a nanocapsule or a nanoparticle of the invention has a diameter of 10 nm-100 nm. In another embodiment, the present invention further provides that a nanocapsule or a nanoparticle of the invention has a diameter of 5 nm-80 nm. In another embodiment, the present invention further provides that a nanocapsule or a nanoparticle of the invention has a diameter of 10 nm-70 nm. In another embodiment, the present invention further provides that a nanocapsule or a nanoparticle of the invention has a diameter of 20 nm-60 nm.

In another embodiment, the present invention further provides that a core is devoid of a low molecular weight surfactant or is substantially free of such a surfactant. In another embodiment, the present invention further provides that the active substance such as a sparingly water soluble substance is carried throughout the system properly and is released at the proper time and location. In another embodiment, the nanocapsules or nanoparticles of the invention are uniformly dispersed in water as an emulsion or within an emulsion.

In another embodiment, the present invention further provides that in its free form, the bioactive compound has maximal aqueous solubility below 5 g/l (water). In another embodiment, the present invention further provides that in its free form, the bioactive compound has maximal aqueous solubility below 3 g/l (water). In another embodiment, the present invention further provides that in its free form, the bioactive compound has maximal aqueous solubility below 2 g/l (water). In another embodiment, the present invention further provides that in its free form, the bioactive compound has maximal aqueous solubility below 1.5 g/l (water). In another embodiment, the present invention further provides that in its free form, the bioactive compound has maximal aqueous solubility below 0.5 g/l (water). In another embodiment, the present invention further provides that in its free form, the bioactive compound has maximal aqueous solubility below 0.1 g/l (water).

In another embodiment, the present invention further provides that the bioactive compound is an amino-acid or a peptide. In another embodiment, the present invention further provides that the bioactive compound is a non-polar amino-acid or a peptide. In another embodiment, the present invention further provides that the bioactive compound is a vitamin. In another embodiment, the present invention further provides that the bioactive compound is an oil-soluble vitamin. In another embodiment, the present invention further provides that the bioactive compound is a polyunsaturated fatty acid. In another embodiment, the present invention further provides that the bioactive compound is an antioxidant. In another embodiment, the present invention further provides that the bioactive compound is phytochemical. In another embodiment, the present invention further provides that the bioactive compound is an ester of any aforementioned compound described herein. In another embodiment, the bioactive compound is a lipid. In another embodiment, the bioactive compound is a phospholipid. In another embodiment, the bioactive compound is a glycolipid. In another embodiment, the bioactive compound is a nutraceutical. In another embodiment, the bioactive compound is a drug. In another embodiment, the bioactive compound is a combination of compounds.

In another embodiment, the bioactive compound is an Omega-3 fatty acid. In another embodiment, the bioactive compound is an Omega-9 fatty acid. In another embodiment, the bioactive compound is an essential fatty acid. In another embodiment, the bioactive compound is an oil, such as, but not limited to, flax seed oil, fish oil or algae oil. In another embodiment, the bioactive compound is Linoleic Acid (LA). In another embodiment, the bioactive compound is Linolenic Acid (LNA). In another embodiment, the bioactive compound comprises LA, LNA, or both. In another embodiment, the bioactive compound is a sterol. In another embodiment, the bioactive compound is a phytosterol. In another embodiment, the bioactive compound is a zoosterol. In another embodiment, the bioactive compound is vitamin D.

In another embodiment, Zidovudine (INN) or azidothymidine (AZT) (also called ZDV) is excluded from the present invention. In another embodiment, Zidovudine (INN) or azidothymidine (AZT) is not the bioactive compound of the present invention. In another embodiment, Itraconazole is excluded from the present invention. In another embodiment, Itraconazole is not the bioactive compound of the present invention. In another embodiment, the present invention is an oral composition. In another embodiment, the present invention does not include topical composition. In another embodiment, the present invention excludes oil based composition. In another embodiment, the present invention excludes lipid based composition.

In another embodiment, a composition as described herein is devoid of Zidovudine (INN) or azidothymidine (AZT) (also called ZDV). In another embodiment, a composition as described herein is devoid of Itraconazole. In another embodiment, a composition as described herein is devoid of an oil based composition. In another embodiment, a composition as described herein is devoid of a lipid based composition.

In another embodiment, the present invention comprises less than 10% w/w lipids or oils. In another embodiment, the present invention comprises less than 5% w/w lipids or oils. In another embodiment, the present invention comprises less than 2.5% w/w lipids or oils. In another embodiment, the present invention comprises less than 1% w/w lipids or oils. In another embodiment, the present invention comprises less than 0.5% w/w lipids or oils. In another embodiment, the present invention comprises less than 0.1% w/w lipids or oils. In another embodiment, the present invention comprises less than 0.05% w/w lipids or oils. In another embodiment, the present invention comprises less than 0.01% w/w lipids or oils.

In another embodiment, the bioactive compound is vitamin A. In another embodiment, the bioactive compound is vitamin E. In another embodiment, the bioactive compound is vitamin K. In another embodiment, the bioactive compound is docosahexaenoic acid (DHA) or an ester thereof. In another embodiment, the bioactive compound is alpha lipoic acid. In another embodiment, the bioactive compound is a carotenoid. In another embodiment, the bioactive compound is beta-Carotene. In another embodiment, the bioactive compound is lutein. In another embodiment, the bioactive compound is lycopene. In another embodiment, the bioactive compound is coenzyme Q10.

In another embodiment, the diameter of the nanoparticle or the nanocapsule is 5 to 200 nm. In another embodiment, the diameter of the nanoparticle or the nanocapsule is 10 to 100 nm. In another embodiment, the diameter of the nanoparticle or the nanocapsule is 10 to 80 nm. In another embodiment, the diameter of the nanoparticle or the nanocapsule is 10 to 50 nm. In another embodiment, the diameter of the nanoparticle or the nanocapsule is 30 to 100 nm. In another embodiment, the diameter of the nanoparticle or the nanocapsule is 60 to 100 nm.

In another embodiment, pectin or sugar-beet pectin is in a pure form. In another embodiment, pectin or sugar-beet pectin is at least 90% pectin. In another embodiment, pectin is in a pure form. In another embodiment, pectin or sugar-beet pectin is at least 95% pectin. In another embodiment, pectin is at least 97% pectin. In another embodiment, pectin or sugar-beet pectin is at least 99% pectin.

In another embodiment, pectin is sugar beet pectin. In another embodiment, pectin is extracted via thermomechanical manipulation of the spent pulp under mildly acidic conditions whereby the hemicellulose complex becomes solubilized. In another embodiment, beet pectin is highly acetylated and contains a moderate degree of feruloyl ester substitution. In another embodiment, beet pectin includes hydrophobic moieties coupled to extensive methyl esterification of D-galacturonic acid.

In another embodiment, beet pectin is obtained from aqueous extracts of spent sugar beet pulp. In another embodiment, pectin as described herein is an emulsifier and/or emulsion stabilizer.

In another embodiment, beet pectin is obtained from pulp or other parenchymal cell-containing plant material that are isolated essentially simultaneously without substantial degradation. In another embodiment, beet pectin is obtained through hydrolysis of spent sugar beet pulp (or other plant material containing parenchymal cells in high proportion) under conditions of moderate pH and high temperature and may include physical shearing. In another embodiment, acidic extraction of sugar beet pulp is accomplished at pH's below about 4.5. In another embodiment, acidic extraction of sugar beet pulp is accomplished at pH's below about 4.0.

In another embodiment, acidic extraction of sugar beet pulp is accomplished at a temperature greater than 120° C. In another embodiment, acidic extraction of sugar beet pulp is accomplished at a temperature between 140 to 180° C. Thus, a sufficient combination of pH, reaction time and reaction temperature which allows the liberation of pectin and arabinogalactan from spent sugar beet pulp (or other parenchymal cell containing plant material) without a substantial degradation.

In another embodiment, the isolation of the pectin components of sugar beet pulp or other parenchymal cell containing plant material may be accomplished in strongly alkaline conditions. Thus, combinations of high (strongly basic) pH, relatively high temperature and relatively short reaction times may be employed for such isolation, enrichment, and/or purification.

In another embodiment, sugar beet pectin is co-isolated with cellulosic components of the materials from which it is derived. In another embodiment, sugar beet pulp, citrus pulp or other parenchymal cell containing material may be treated in such a way as to co-isolate both parenchymal cell cellulose (PCC), and pectin components of those plant materials. In another embodiment, the resulting, combined materials may be useful for any of the methods, and in any of the materials discussed above under appropriate circumstances. In another embodiment, pectin includes blends, mixtures or co-isolates form a natural gum having properties not unlike naturally-occurring gums well known to persons of ordinary skill in the food science art. In another embodiment, compositions of the present invention, include from about 0.01 to about 10.0 wt.-% of sugar beet pectin. In another embodiment, compositions of the present invention, include from about 0.01 to about 1.0 wt.-% of sugar beet pectin.

In another embodiment, the present invention further provides a composition comprising the nanocapsules or the nanoparticles in an aqueous solution. In another embodiment, the present invention further provides that the composition comprising the nanocapsules or the nanoparticles is a nanoemulsion. In another embodiment, the present invention further provides that the aqueous solution is a transparent aqueous liquid. In another embodiment, the present invention further provides that the aqueous solution is a beverage. In another embodiment, the present invention further provides that the aqueous solution is devoid of an additional emulsifier.

In another embodiment, the aqueous solution is transparent. In another embodiment, the aqueous solution comprises at least 70% by weight water. In another embodiment, the aqueous solution comprises at least 75% by weight water. In another embodiment, the aqueous solution comprises at least 85% by weight water. In another embodiment, the aqueous solution comprises at least 90% by weight water. In another embodiment, the aqueous solution comprises at least 95% by weight water. In another embodiment, the aqueous solution comprises at least 98% by weight water.

In another embodiment, the present invention further provides that the composition of the invention is stable for at least 10 to 120 seconds at pH=2 to 8 and at temperature of 65 to 80° C. In another embodiment, the present invention further provides that the composition of the invention is stable for at least 10 to 90 seconds at pH=2 to 8 and at temperature of 70 to 80° C. In another embodiment, the present invention further provides that the composition of the invention is stable for up to 60 seconds at pH=2 to 8 and at temperature of 70 to 75° C. In another embodiment, the present invention further provides that the composition of the invention is stable for at least 60 seconds at pH=2.5 and at a temperature of 72° C.

In another embodiment, the present invention further provides that the composition of the invention is stable at pH=2 to 8 during cooling from a temperature of 90° C. down to 25° C. within 30 min.

In another embodiment, the present invention further provides that the composition of the invention is stable for at least 2 months under appropriate storage conditions. In another embodiment, the present invention further provides that the composition of the invention is stable for at least 6 months under appropriate storage conditions. In another embodiment, the present invention further provides that the composition of the invention is stable for at least 12 months under appropriate storage conditions. In another embodiment, the present invention further provides that the composition of the invention is stable for at least 90 hours at pH=2-8 and at temperature of 4 to 35° C. In another embodiment, the present invention further provides that the composition of the invention is stable for up to 40 hours at pH 2 to 8 and at temperature of 20 to 30° C. In another embodiment, the present invention further provides that the composition of the invention is stable for at least 24 to 36 hours at pH=2.5 and at temperature of 23 to 27° C. In another embodiment, the present invention further provides that the composition of the invention is stable for at least 24 hours at pH=2.5 and a temperature of 25° C. In another embodiment, the present invention further provides that the composition of the invention is stable for up to 24 hours at pH=2.5 and a temperature of 25° C.

In another embodiment, the phrase: "pectin and bioactive compound" is synonymous with the phrase "a bioactive compound bound to pectin".

In another embodiment, the present invention further provides that the process of making a composition of the invention comprises the steps of: (1) mixing pectin and a bioactive compound in an aqueous solution; (2) freeze-drying or spray drying the solution comprising pectin and a bioactive compound, thus obtaining a freeze-dried composition of pectin and a bioactive compound; (2) re-suspending the freeze-dried composition of pectin and a bioactive compound in an aqueous solution.

In another embodiment, the present invention further provides that the bioactive compound is present at a concentration of 0.01 microgram/ml to 10 mg/ml. In another embodiment, the present invention further provides that the bioactive compound is present at a concentration of 0.5 mg/ml to 5 mg/ml. In another embodiment, the present invention further provides that the bioactive compound is present at a concentration of 1 microgram/ml to 1 mg/ml. In another embodiment, the present invention further provides that the bioactive compound is present at a concentration of 100 microgram/ml to 1 mg/ml. In another embodiment, the present invention further provides that the bioactive compound is present at a concentration of 100 microgram/ml to 0.5 mg/ml. In another embodiment, the present invention further provides that the bioactive compound is present at a concentration of 0.5 mg/ml to 1 mg/ml. In another embodiment, the present invention further provides that the bioactive compound is present at a concentration of 0.1 mg/ml to 1 mg/ml. In another embodiment, the present invention further provides that the bioactive compound is present at a concentration of 0.5 mg/ml to 1 mg/ml.

In another embodiment, the present invention further provides that the nanoparticles and/or nanocapsules or any composition comprising the nanoparticles and/or nanocapsules is/are devoid of a low molecular weight surfactant. In another embodiment, the present invention further provides that the nanoparticles and/or nanocapsules or any composition comprising the nanoparticles and/or nanocapsules is/are devoid of a low molecular weight surfactant.

In another embodiment, a composition of the invention is devoid of an organic solvent. In another embodiment, a composition of the invention is devoid of alcohol. In another embodiment, a composition of the invention in the form of a solution is free of a low molecular weight emulsifier. In another embodiment, a composition of the invention comprises a water miscible solvent such as ethanol or DMSO in a trace amount.

In another embodiment, a composition of the invention comprises less than 5% in weight a water miscible solvent such as ethanol. In another embodiment, a composition of the invention comprises less than 2.5% in a water miscible solvent such as ethanol. In another embodiment, a composition of the invention comprises less than 1% in weight of a water miscible solvent such as ethanol. In another embodiment, a composition of the invention comprises less than 0.5% in weight a water miscible solvent such as ethanol. In another embodiment, a composition of the invention comprises less than 0.1% in weight a water miscible solvent such as ethanol.

In another embodiment, a composition of the invention is devoid of an alcohol. In another embodiment, nanoparticles and/or nanocapsules are formed and the bioactive is entrapped simultaneously in one stage. In another embodiment, the process of making the nanoparticles and/or nanocapsules of the invention is devoid of heating.

In another embodiment, the present invention further provides a method of supplementing a subject with a bioactive compound of the invention, comprising the step of administering to the subject a composition comprising: the aqueous liquid, a bioactive compound, and pectin or sugar-beet pectin, thereby supplementing a subject with a bioactive compound. In another embodiment, the aqueous liquid comprises a bioactive compound bound to pectin or sugar-beet pectin, thereby supplementing a subject with a bioactive compound. In another embodiment, an aqueous liquid is a transparent aqueous liquid comprising nanocapsules or nanoparticles of the invention.

In another embodiment, a subject is a human. In another embodiment, a subject is an infant. In another embodiment, a subject is a toddler. In another embodiment, a subject is a pet. In another embodiment, a subject is a farm animal. In another embodiment, a subject is a rodent.

In another embodiment, the present invention further provides a method of supplementing a subject with a bioactive compound, such as a nutraceutical or a drug, comprising the step of administering to the subject a composition comprising: an aqueous liquid, a bioactive compound, and pectin or sugar-beet pectin, thereby supplementing a subject with a bioactive compound. In another embodiment, the composition comprising a bioactive is administered orally. In another embodiment, the bioactive is any non-toxic food component which has demonstrated health benefits. In another embodiment, the bioactive is any sparingly water soluble, non-toxic food component, which has demonstrated health benefits.

In another embodiment, the bioactive nutraceutical is an omega-3 fatty acid such as α-linolenic acid (ALA) and/or eicosapentaenoic acid (EPA). In another embodiment, the nutraceutical is sea food PUFA such as eicosapentaenoic acid (EPA) and/or docosahexaenoic acid (DHA). In another embodiment, the nutraceutical is DHASCO (DHA single cell oil). In another embodiment, the nutraceutical is a monounsaturated fatty acid (MUFAs) such as oleic acid. In another embodiment, the nutraceutical is medium-chain fatty acids (MCFAs) and/or medium-chain triacylglycerol (MCT). In another embodiment, the nutraceutical is conjugated linoleic acid (CLA) and/or γ-linolenic acid. In another embodiment, the nutraceutical is diacylglycerol (DAG) oil. In another embodiment, the nutraceutical is a triacyl glycerol (TAG). In another embodiment, the nutraceutical is a phospholipid.

In another embodiment, the present invention further provides a method of supplementing a subject with a bioactive compound of the invention, comprising the step of administering to the subject a nano-emulsion composition comprising: an aqueous liquid, a bioactive compound, and pectin or sugar-beet pectin, thereby supplementing a subject with a bioactive compound.

In another embodiment, the subject is afflicted with a disease requiring essential fatty acids support. In another embodiment, the subject is afflicted with a cardiovascular disease. In another embodiment, the subject is afflicted with a reproductive disease. In another embodiment, the subject is afflicted with an immune disease. In another embodiment, the subject is afflicted with a nervous system disease.

In another embodiment, the subject is an infant and the composition is used for supplementing required essential fatty acids for neural development and maturation of sensory systems. In another embodiment, the composition is used for supplementing required essential fatty acids/lipids for treating health conditions such as but not limited to: skin diseases and pathologies, hair loss, behavioral changes, failure to heal wounds, miscarriages, arthritic conditions, increased cholesterol, growth retardation, depression, dyslexia, impaired vision, learning problems in children, heart attacks, cancer, insulin resistance, asthma, lupus, schizophrenia, accelerated aging, stroke, obesity, diabetes, ADHD, and alzheimer's disease, etc.

In another embodiment, the bioactive compound is an eicosanoid, an arachidonic acid, or any derivative thereof. In another embodiment, a bioactive compound of the invention such as prostaglandin E 2 (PGE 2) is used to suppress the immune response of a subject. In another embodiment, a bioactive compound of the invention such as PGE2 is used to promote cell growth of a subject. In another embodiment, a bioactive compound of the invention such as PGE2 is used as a vasodilator. In another embodiment, a bioactive compound of the invention such as PGE2 is used to induce and/or enhance the formation of anti-inflammatory lipoxins in a subject.

In another embodiment, a bioactive compound of the invention such as Prostaglandin I(2) (PGI(2)) is used to suppress the immune response of a subject. In another embodiment, a bioactive compound of the invention such as PGI(2) is used to inhibit platelet aggregation in a subject. In another embodiment, a bioactive compound of the invention such as PGI(2) is used as a potent vasodilator.

In another embodiment, a bioactive compound of the invention such as Thromboxane A2 (TXA2) is used to suppress the immune response of a subject. In another embodiment, a bioactive compound of the invention such as TXA2 is used as a vasoconstrictor.

In another embodiment, a bioactive compound of the invention such as Prostaglandin D2 (PGD2) is used to inhibit platelet aggregation in a subject. In another embodiment, a bioactive compound of the invention such as PGD2 is used as a sleep promoter in a subject. In another embodiment, a bioactive compound of the invention such as PGD2 is used as a vasodilator.

In another embodiment, a bioactive compound of the invention such as 12-hydroxy-5,8,10,14-eicosatetraenoic acid (12-HETE) is used as a neutrophil chemo-attractant. In another embodiment, a bioactive compound of the invention such as 12-HETE is used as a stimulator of glucose-induced insulin secretion. In another embodiment, a bioactive compound of the invention such as 15-Hydroxyeicosatetraenoic acid (15-HETE) is used as an inhibitor of 5- and 12-lipoxygenase. In another embodiment, a bioactive compound of the invention such as Lipoxin A is used as a chemo-attractant. In another embodiment, a bioactive compound of the invention such as Lipoxin B is used as an inhibitor of NK cell activity.

In another embodiment, a bioactive compound of the invention such as a fatty acid is used, for example, in the treatment of chronic diseases such as but not limited to: CHD, obesity, diabetes, and specific types of cancers as are known to one of average skill in the art. In another embodiment, a bioactive compound of the invention is used, for example, in the treatment of vitamin D deficiency.

In another embodiment, the invention further provides a kit comprising the nanoparticles or nanocapsules of the invention in liquid or dry form and dosing, mixing, and/or formulating instructions. In another embodiment, the invention further provides a kit comprising the nanoparticles or nanocapsules of the invention and dosing, mixing, and/or formulating instructions with an aqueous solution as described herein. In another embodiment, the invention further provides a kit comprising the nanoparticles or nanocapsules, an aqueous solution as described herein and dosing, mixing, and/or formulating instructions.

In one embodiment, compositions of the present invention are presented in a pack or dispenser device, such as an FDA approved kit, which contain one or more unit dosage forms containing the nanoparticles or nanocapsules. In one embodiment, the pack, for example, comprise metal or plastic foil, such as a blister pack. In one embodiment, the pack or dispenser device is accompanied by instructions for administration. In one embodiment, the pack or dispenser is accommodated by a notice associated with the container in a form prescribed by a governmental agency regulating the manufacture, use or sale of pharmaceuticals and/or nutraceuticals, which notice is reflective of approval by the agency of the form of the compositions or human or veterinary administration. Such notice, in one embodiment, is labeling approved by the U.S. Food and Drug Administration for prescription drugs or of an approved product insert.

In one embodiment, toxicity and therapeutic efficacy of the nanoparticles or nanocapsules described herein can be determined by standard pharmaceutical procedures in vitro, in cell cultures or experimental animals. In one embodiment, the data obtained from these in vitro and cell culture assays and animal studies can be used in formulating a range of dosage for use in human. In one embodiment, the dosages vary depending upon the dosage form employed and the route of administration utilized. In one embodiment, the exact formulation, route of administration and dosage can be chosen by the individual physician in view of the patient's condition. [See e.g., Fingl, et al., (1975) "The Pharmacological Basis of Therapeutics", Ch. 1 p. 1].

In one embodiment, depending on the severity and responsiveness of the condition to be treated, dosing can be of a single or a plurality of administrations, with course of treatment lasting from several days to several weeks or until cure is effected or diminution of the disease state is achieved.

In one embodiment, the amount of a composition to be administered will, of course, be dependent on the subject being treated, the severity of the affliction, the manner of administration, the judgment of the prescribing physician, etc.

In one embodiment, the nanocapsules and/or nanoparticles of the present invention can be provided to the individual per se (as a powder for example). In one embodiment, the nanocapsules and/or nanoparticles of the present invention can be provided to the individual as part of a pharmaceutical composition where it is mixed with a pharmaceutically acceptable carrier.

In one embodiment, a "pharmaceutical composition" refers to a preparation of one or more nanocapsules and/or nanoparticles described herein with other chemical components such as physiologically suitable carriers and excipients. The purpose of a pharmaceutical composition is to facilitate administration of nanocapsules and/or nanoparticles to an organism.

In one embodiment, the phrases "physiologically acceptable carrier" and "pharmaceutically acceptable carrier", which are interchangeably used, refer to a carrier or a diluent that does not cause significant irritation to an organism and does not abrogate the biological activity and properties of the administered compound. An adjuvant is included under these phrases. In one embodiment, one of the ingredients included in the pharmaceutically acceptable carrier can be for example polyethylene glycol (PEG), a biocompatible polymer with a wide range of solubility in both organic and aqueous media (Mutter et al. (1979).

In one embodiment, "excipient" refers to an inert substance added to a pharmaceutical composition to further facilitate administration of nanocapsules and/or nanoparticles. In one embodiment, excipients include calcium carbonate, calcium phosphate, various sugars and types of starch, cellulose derivatives, gelatin, vegetable oils and polyethylene glycols.

Techniques for formulation and administration of drugs are found in "Remington's Pharmaceutical Sciences," Mack Publishing Co., Easton, Pa., latest edition, which is incorporated herein by reference.

In one embodiment, suitable routes of administration, for example, include oral, rectal, transmucosal, transnasal, intestinal or parenteral delivery, including intramuscular, subcutaneous and intramedullary injections as well as intrathecal, direct intraventricular, intravenous, intraperitoneal, intranasal, or intraocular injections.

Oral administration, in one embodiment, comprises a unit dosage form comprising solutions, suspensions, emulsions and the like. Such unit dosage forms comprise a safe and effective amount of the desired nanocapsules and/or nanoparticles.

Peroral compositions, in some embodiments, comprise liquid solutions, emulsions, suspensions, and the like.

In some embodiments, compositions for use in the methods of this invention comprise solutions or emulsions, which in some embodiments are aqueous solutions or emulsions comprising a safe and effective amount of the nanocapsules and/or nanoparticles of the present invention and optionally, other compounds. In some embodiments, the compositions comprise from about 0.01% to about 10.0% w/v of a subject compound, more preferably from about 0.1% to about 2.0.

Further, in another embodiment, the pharmaceutical compositions are administered topically to body surfaces, and are thus formulated in a form suitable for topical administration. Suitable topical formulations include gels, ointments, creams, lotions, drops and the like. For topical administration, the nanocapsules and/or nanoparticles of the present invention are combined with an additional appropriate therapeutic agent or agents, prepared and applied as solutions, suspensions, or emulsions in a physiologically acceptable diluent with or without a pharmaceutical carrier.

In one embodiment, pharmaceutical compositions of the present invention are manufactured by processes well known in the art, e.g., by means of conventional mixing, dissolving, granulating, dragee-making, levigating, emulsifying, encapsulating, entrapping or lyophilizing processes.

In one embodiment, injectables, of the invention are formulated in aqueous solutions. In one embodiment, injectables, of the invention are formulated in physiologically compatible buffers such as Hank's solution, Ringer's solution, or physiological salt buffer. In some embodiments, for transmucosal administration, penetrants appropriate to the barrier to be permeated are used in the formulation. Such penetrants are generally known in the art.

In one embodiment, the preparations described herein are formulated for parenteral administration, e.g., by bolus injection or continuous infusion. In some embodiments, formulations for injection are presented in unit dosage form, e.g., in ampoules or in multidose containers with optionally, an added preservative. In some embodiments, compositions are suspensions, solutions or emulsions in aqueous vehicles, and contain formulatory agents such as suspending, stabilizing and/or dispersing agents.

The compositions also comprise, in some embodiments, preservatives, such as benzalkonium chloride and thimerosal and the like; chelating agents, such as edetate sodium and others; buffers such as phosphate, citrate and acetate; tonicity agents such as sodium chloride, potassium chloride, glycerin, mannitol and others; antioxidants such as ascorbic acid, acetylcystine, sodium metabisulfote and others; aromatic agents; viscosity adjustors, such as polymers, including cellulose and derivatives thereof; and polyvinyl alcohol and acid and bases to adjust the pH of these aqueous compositions as needed. The compositions also comprise, in some embodiments, local anesthetics or other actives. The compositions can be used as sprays, mists, drops, and the like.

In another embodiment, the pharmaceutical composition is delivered in a controlled release system formulated for intravenous infusion, implantable osmotic pump, transdermal patch, or other modes of administration. In one embodiment, a pump is used (see Langer, supra; Sefton, CRC Crit. Ref. Biomed. Eng. 14:201 (1987); Buchwald et al., Surgery 88:507 (1980); Saudek et al., N. Engl. J. Med. 321:574 (1989). Other controlled release systems are discussed in the review by Langer (Science 249:1527-1533 (1990).

In some embodiments, the nanocapsules and/or nanoparticles are in powder form and possibly in kits for constitution with a suitable vehicle, e.g., sterile, pyrogen-free water based solution or a beverage, before use. Compositions are formulated, in some embodiments, for atomization and inhalation administration. In another embodiment, compositions are contained in a container with attached atomizing means.

In one embodiment, the preparation of the present invention is formulated in rectal compositions such as suppositories or retention enemas, using, e.g., conventional suppository bases such as cocoa butter or other glycerides.

In one embodiment, nanocapsules or nanoparticles of the invention are made by a process comprising the steps of: preparing solution 1 comprising: (a) dissolving pectin or sugar-beet pectin in water at a concentration of 0.1-100 g/L and typically at a concentration of 0.7 to 1.5 g/L; (b) stirring/mixing the solution for 20 minutes to 20 hours and typically for 0.5 to 2 hours at 4 to 40° C. and typically at 25° C.; (c) after complete dissolution the solution is filtered through a filter having a cutoff of 0.1 to 2 micron; preparing solution 2 comprising: (a) dissolving the bioactive compound in a water-miscible organic food grade solvent (typically absolute ethanol), or a water-miscible solvent for pharmaceutical applications (e.g. DMSO); combining solution 1 and solution 2 by drop-wise or slowly adding solution 2 into solution 1 and vigorous stirring. In another embodiment, vigorous stirring is performed by utilizing vortex.

In another embodiment, the final concentration of the organic solvent in the obtained aqueous solution is 0.001 to 20% and more typically 0.1 to 2%. In another embodiment, the final concentration of the organic solvent in the obtained aqueous solution is 0.01 to 10%. In another embodiment, the final concentration of the organic solvent in the obtained aqueous solution is 0.01 to 1%. In another embodiment, the final concentration of the organic solvent in the obtained aqueous solution is 0.1 to 5%. In another embodiment, the final concentration of the organic solvent in the obtained aqueous solution is 0.1 to 5%. In another embodiment, the final concentration of the organic solvent in the obtained aqueous solution is 0.1 to 1%. In some embodiments, the organic solvent is completely removed by evaporation and/or drying.

In another embodiment, the combined solution 1 and solution 2 is further filtered through a filter having cutoff of 0.1 to 15 micron. In another embodiment, the filter of the invention has a cutoff of 0.2 to 5 micron. In another embodiment, the filter of the invention has a cutoff of 0.1 to 0.8 micron. In another embodiment, the filter of the invention has a cutoff of 0.2 to 0.5 micron. In another embodiment, the filter of the invention has a cutoff of 0.1 to 0.45 micron.

In another embodiment, the combined mix of solution 1 and solution 2, filtered or unfiltered, is further dried according to methods known in the art and a powder is obtained. In another embodiment, the combined mix of solution 1 and solution 2, filtered or unfiltered, is freeze dried. In another embodiment, a cryoprotectant (e.g. trehalose or maltodextrin) is further utilized. In another embodiment, the combined mix of solution 1 and solution 2, filtered or unfiltered, is quench frozen (e.g. by liquid nitrogen). In another embodiment, a powder comprising or consisting the resulting nanocapsules or nanoparticles of the invention is obtained. In another embodiment, a powder comprising or consisting the resulting nanocapsules or nanoparticles of the invention is reconstituted by adding a known amount of the powder to an aqueous solution, while stirring, thereby obtaining a composition of the invention.

EXAMPLES

Example 1: Sugar Beet Pectin-Based Delivery Systems for Food Enrichment with Nutraceuticals to Improve Human Health Enhancing health-promoting properties of food may be attainable by incorporating nutraceutical delivery systems.

To this end, nanoencapsulation offers several advantages, including stabilization and protection of hydrophobic nutraceuticals even in transparent beverages, as well as their controlled and targeted release in the human gastrointestinal tract. Sugar beet pectin, a by-product of sugar production from sugar beet, is a readily sourced, naturally occurring dietary fiber with high emulsifying capacity. The exact underlying molecular traits delineating sugar beet pectin functionality are still obscure.

Figure 2:
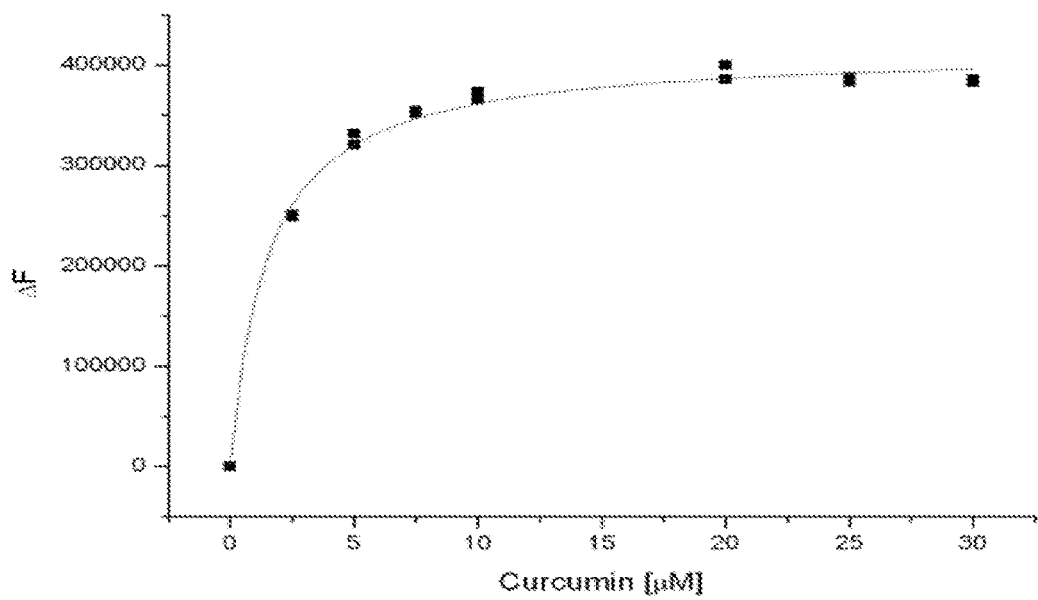
FIG. 2. Is a graph presenting the results of a curcumin—SBP binding assay ($k_b=(6.74+0.5)-10^5 M^{-1}$), measured by fluorescence quenching of the tyrosine (Tyr) residue in the protein fraction of SBP, using excitation wavelength of 280 nm, and emission at 350 nm. Fluorescence was measured at a constant SBP concentration (0.25 mg/ml of 3 mM PBS, pH6.8).

Sugar Beet Pectin (SBP) Critical Micellization Concentration (CMC) and Curcumin Binding Constant The self-assembly of SBP was studied using pyrene—a hydrophobic domain probe (Aguiar, J.; Carpena, P.; Molina-Bolivar, J. A.; Ruiz, C. C. On the determination of the critical micelle concentration by the pyrene 1:3 ratio method Journal of Colloid and Interface Science 2003, 258, (1), 116-122.). The ratio between the emission intensity of the third (~383 nm) and first (~373 nm) peaks (I3/I1) (excitation at 338 nm) were measured at rising SBP concentration (C). The critical micellization concentration (CMC) was estimated from the onset of rise in the I3/I1 vs SBP concentration, to be ~1 mg/ml. The binding constant obtained (FIG. 1) using a Langmuir model was $K_b=(6.74\pm0.5)*10^5$ $M^{-1}$, showing high affinity, and suggesting that SBP is an excellent entrapping agent for delivery of hydrophobic bioactives, e.g. curcumin (FIG. 2).

SBP Protects Curcumin During Simulated Product Shelf Life

Figure 3:
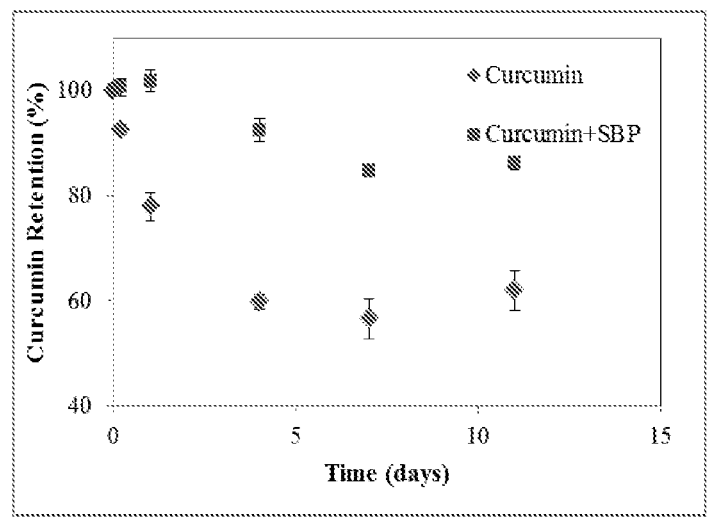
FIG. 3. Is a graph depicting the SBP protective effect. Residual percentage of curcumin (with respect to time 0) during simulated shelf life, without and with protection by SBP. Curcumin was determined by absorbance at 415 nm (maximal absorbance of curcumin) as determined by a UV-Visible light spectrophotometer.

As can be seen in FIG. 3, unprotected curcumin decreased by approximately 40% over a period of 11 days, while curcumin encapsulated in SBP showed only a 15% decrease. These results indicate a remarkable protection of curcumin by SBP, suggesting that SBP may be a useful protective nanoencapsulation agent for enriching food & beverage products with curcumin, and possibly similar hydrophobic nutraceuticals.

CONCLUSIONS

SBP showed a CMC of about 1 mg/ml. Binding of curcumin to SBP was found to be of high affinity ($k_b=(6.74\pm0.5)\cdot10^5 M^{-1}$), suggesting that SBP has very good binding properties, useful for effective delivery of important hydrophobic bioactives.

Moreover, while unprotected curcumin decreased by approximately 40% over a period of 11 days, curcumin encapsulated in SBP showed only a 15% decrease. These results indicate a remarkable protection of curcumin by SBP, suggesting that SBP may be a useful protective nanoencapsulation agent for enriching food & beverage products with curcumin, and possibly similar hydrophobic nutraceuticals.

What is claimed is:

1. A nanoparticle comprising: (a) sugar-beet pectin; and (b) a bioactive compound bound to said sugar-beet pectin, wherein said bioactive compound is a compound having a maximal aqueous solubility below 1 g/l in its free form, wherein said nanoparticle: has a diameter of 10 to 100 nm, is devoid of a low molecular weight surfactant and has less than 5% by weight a water miscible solvent.

2. The nanoparticle of claim 1, wherein said bioactive compound is an oil-soluble vitamin, a polyunsaturated fatty acid or its ester, an antioxidant, or a phytochemical.

3. The nanoparticle of claim 1, wherein said bioactive compound is an essential fatty acid or its ester, an Omega-3 fatty acid or its ester, docosahexaenoic acid (DHA) or its ester, eicosapentaenoic acid (EPA) or its ester, or any combination thereof.

4. The nanoparticle of claim 1, wherein said bioactive compound is: vitamin D, vitamin E, vitamin A, vitamin K, curcumin; coenzyme Q-10, a carotenoid, an isoflavone or polyphenol, or any combination thereof.

5. The nanoparticle of claim 1, wherein said sugar-beet pectin is an unfractioned sugar-beet pectin.

6. A dry powder comprising the nanoparticle of claim 1.

7. A composition comprising an aqueous liquid, and a nanoparticle, said nanoparticle comprises: (a) sugar-beet pectin; and (b) a bioactive compound bound to said sugar-beet pectin, wherein said nanoparticle: has a diameter of 10 to 100 nm, is devoid of a low molecular weight surfactant and has less than 5% by weight a water miscible solvent.

8. The composition of claim 7, wherein said aqueous liquid is a beverage.

9. The composition of claim 7, devoid of an additional emulsifier.

10. The composition of claim 7, wherein said composition is a nano-emulsion or a nano-dispersion.

11. The composition of claim 7, wherein said bioactive compound is present at a concentration of 0.01 microgram/ml to 10 mg/ml.

12. The composition of claim 7, wherein said bioactive compound is a compound having maximal aqueous solubility below 1 g/l.

13. The composition of claim 7, wherein said bioactive compound is an oil-soluble vitamin, a polyunsaturated fatty acid or its ester, an antioxidant, or a phytochemical.

14. The composition of claim 7, wherein said composition is a transparent beverage.

15. A kit comprising the dry powder of claim 6 and mixing instructions for obtaining the composition comprising an aqueous liquid, and a nanoparticle, said nanoparticle comprises: (a) sugar-beet pectin; and (b) a bioactive compound bound to said sugar-beet pectin, wherein said nanoparticle: has a diameter of 10 to 100 nm, is devoid of a low molecular weight surfactant and has less than 5% by weight a water miscible solvent.

* * * * *